United States Patent [19]
Doherty et al.

[11] Patent Number: 5,610,177
[45] Date of Patent: Mar. 11, 1997

[54] ACYLATED AMINO ACIDS AS ENDOTHELIN ANTAGONISTS

[75] Inventors: Annette M. Doherty, Ann Arbor; Harriet W. Hamilton, Chelsea; James S. Kaltenbronn; John Quin, III, both of Ann Arbor, all of Mich.

[73] Assignee: Warner-Lambert Company, Morris Plains, N.J.

[21] Appl. No.: 287,389

[22] Filed: Aug. 8, 1994

[51] Int. Cl.$^6$ .................. C07D 209/20; C07D 403/06; C07D 401/06; C07D 413/06; A61K 3/405; A61K 3/445; A61K 31/535; A61K 31/495

[52] U.S. Cl. .................. 514/419; 514/422; 514/323; 514/235.2; 514/253; 548/496; 548/468; 546/201; 544/143; 544/373

[58] Field of Search .................. 548/496, 468; 514/419, 422, 323, 235.2, 253; 546/201; 544/143, 373

[56] References Cited

FOREIGN PATENT DOCUMENTS

436189A1  7/1991  European Pat. Off. .

OTHER PUBLICATIONS

Watanabe, T. et al., *Nature*, 1990, 344:114.
Margulies, K.B., et al., *Circulation*, 1990, 82:2226.
Kon, V., et al., *J. Clin Inves*, 1989, 83:1762.
Perico, N., et al., *J. Amer Soc Nephrol*, 1990, 1:1, 76–82.
Koshi, T., et al., *Chem Pharm Bull*, 1991, 39:5, 1295–1297.
Miyamori, I., et al., *Clinical & Experimental Pharmacology and Physiology*, 1990, 17:691–696.
Ohno, A., *J of Tokyo Women's Medical College*, 1991, 61:10–11, 951–959.
Lerman, A., et al., *Circulation*, 1991, 83:1808–1814.
Rodeheffer, R.J., et al., *American J of Hypertension*, 1991, 4:5(2), 9A–10A.
Arai, H., et al., *Nature*, 1990, 348:730–732.
Lin, H.Y., et al., *Proc Natl Acad Sci USA*, 1991, 88:3185–3189.
Sakamoto, A., et al., *Biochemical & Biophysical Research Communications*, 1991, 178:2, 656–663.
Hosoda, K., et al., *FEBS Lett.*, 1991, 287:1.2, 23–26.
Takayanagi, R., et al., *FEBS Lett.*, 1991, 282:1, 103–106.
Panek, R.L., et al., *Biochemical & Biophysical Research Communications*, 1992, 183:2, 566–571.
Saeki, T., et al., *Biochemical & Biophysical Research Communications*, 1991, 179:1, 286–292.
Nakagawa, K., et al., *Nippon Hifuka Gakkai Zasshi*, 1990, 100:14, 1453–1456.
Noguchi, K., et al., *Am Rev Respir Dis*, 1992, 145:4(2), A858.
Clark, B.A., et al., *Am J Obstet Gynecol*, 1992, 166:3, 962–968.
Pittet, J–F, et al., *Ann Surg*, 1991, 213:3, 261–264.
Gandhi, C.R., et al., *J of Biological Chemistry*, 1990, 265:29, 17432–17435.
Collier, A., et al., *Diabetes Care*, 1992, 15:8, 1038–1040.
Basil, M.K., et al., *J. Hypertension*, 1992, 10:4, S49.
Han, S–P, et al., *Life Sciences*, 1990, 40:767–775.
Nikolov, R.K., et al., *Drugs of Today*, 1992, 28:5, 303–310.
Lerman, A., et al., *New England J of Medicine*, 1991, 325:14, 997–1001.
Kanno, K., *JAMA*, 1990, 264:22, 2868.
Zamora, M.R., et al., *Lancet*, 1990, 336:1144–1147.
Tahara, A., et al., *Metabolism*, 1991, 40:12, 1235–1237.
Stewart, D.J., et al., *Annals of Internal Medicine*, 1991, 114:6, 464–469.
Yasuda, M., et al., *Amer Heart J*, 1990, 801–806.
Stewart, J.T., et al., *Br Heart J*, 1991, 66:7–9.
Lopez–Farre, A., et al., *J of Physiology*, 1991, 444:513–522.
Stockenhuber, F., et al., *Clinical Science*, 1992, 82:255–258.
Miura, S., et al., *Digestion*, 1991, 48:163–172.
Masuda, E., et al., *Am J Physiol*, 1992 262:G785–G790.
Murch, S.H., et al., *Lancet*, 1992, 339:381–384.
Clozel, M., et al., *Nature*, 1993, 365:759–761.
Clozel, M., et al., *Life Sciences*, 1993, 52:825–834.
Stein, P.D., et al., *J Med Chem*, 1994, 37:3, 329–331.
Allen, C.F.H., et al., *Canadian Journal of Research*, 1932, 6:605–613.
Allen, C.F.H., et al., *Canadian Journal of Research*, 1933, 8:137–141.
Allen, C.F.H., et al., *Canadian Journal of Research*, 1934, 11:382–394.
Allen, C.F.H., et al., *Canadian Journal of Chemistry*, 1956, 34:926–930.

Primary Examiner—David B. Springer
Attorney, Agent, or Firm—Elizabeth M. Anderson

[57] ABSTRACT

Novel acylated amino acids which are antagonists of endothelin are described. Methods for their preparation and pharmaceutical compositions containing them are also included. The compounds are expected to be useful in treating elevated levels of endothelin, acute and chronic renal failure, hypertension, myocardial infarction, myocardial ischemia, cerebral vasospasm, cirrhosis, septic shock, congestive heart failure, endotoxic shock, subarachnoid hemorrhage, arrhythmias, asthma, preeclampsia, atherosclerotic disorders including Raynaud's disease and restenosis, angina, cancer, pulmonary hypertension, ischemic disease, gastric mucosal damage, hemorrhagic shock, ischemic bowel disease, diabetes, head injury, and stroke.

12 Claims, No Drawings

ACYLATED AMINO ACIDS AS ENDOTHELIN ANTAGONISTS

BACKGROUND OF THE INVENTION

The present invention relates to novel antagonists of endothelin useful as pharmaceutical agents, to methods for their production, to pharmaceutical compositions which include these compounds and a pharmaceutically acceptable carrier, and to pharmaceutical methods of treatment. More particularly, the compounds of the present invention are antagonists of endothelin useful in treating elevated levels of endothelin, acute and chronic renal failure, hypertension, myocardial infarction and myocardial ischemia, cerebral vasospasm, cirrhosis, septic shock, congestive heart failure, endotoxic shock, subarachnoid hemorrhage, arrhythmias, asthma, preeclampsia, atherosclerotic disorders including Raynaud's disease and restenosis, angina, cancer, pulmonary hypertension, ischemic disease, gastric mucosal damage, hemorrhagic shock, ischemic bowel disease, and diabetes.

Also, the compounds will be useful in cerebral ischemia or cerebral infarction resulting from a range of conditions such as thromboembolic or hemorrhagic stroke, cerebral vasospasm, head injury, hypoglycemia, cardiac arrest, status epilepticus, perinatal asphyxia, anoxia such as from drowning, pulmonary surgery, and cerebral trauma.

Endothelin-1 (ET-1), a potent vasoconstrictor, is a 21 amino acid bicyclic peptide that was first isolated from cultured porcine aortic endothelial cells. Endothelin-1, is one of a family of structurally similar bicyclic peptides which include; ET-2, ET-3, vasoactive intestinal contractor (VIC), and the sarafotoxins (SRTXs).

Endothelin is involved in many human disease states.

Several in vivo studies with ET antibodies have been reported in disease models. Left coronary artery ligation and reperfusion to induce myocardial infarction in the rat heart, caused a 4- to 7-fold increase in endogenous endothelin levels. Administration of ET antibody was reported to reduce the size of the infarction in a dose-dependent manner (Watanabe T., et al., "Endothelin in Myocardial Infarction," *Nature* (Lond.), 344:114 (1990)). Thus, ET may be involved in the pathogenesis of congestive heart failure and myocardial ischemia (Margulies K. B., et al., "Increased Endothelin in Experimental Heart Failure," *Circulation*, 82:2226 (1990)).

Studies by Kon and colleagues using anti-ET antibodies in an ischemic kidney model, to deactivate endogenous ET, indicated the peptide's involvement in acute renal ischemic injury (Kon V., et al., "Glomerular Actions of Endothelin In Vivo," *J. Clin. Invest.*, 83:1762 (1989)). In isolated kidneys, preexposed to specific antiendothelin antibody and then challenged with cyclosporine, the renal perfusate flow and glomerular filtration rate increased, while renal resistance decreased as compared with isolated kidneys preexposed to a nonimmunized rabbit serum. The effectiveness and specificity of the anti-ET antibody were confirmed by its capacity to prevent renal deterioration caused by a single bolus dose (150 pmol) of synthetic ET, but not by infusion of angiotensin II, norepinephrine, or the thromboxane $A_2$ mimetic U-46619 in isolated kidneys (Perico N., et al., "Endothelin Mediates the Renal Vasoconstriction Induced by Cyclosporine in the Rat," *J. Am. Soc. Nephrol.*, 1:76 (1990)).

Others have reported inhibition of ET-1 or ET-2-induced vasoconstriction in rat isolated thoracic aorta using a monoclonal antibody to ET-1 (Koshi T., et al., "Inhibition of Endothelin (ET)-1 and ET-2-Induced Vasoconstriction by Anti-ET-1 Monoclonal Antibody," *Chem. Pharm. Bull.*, 39:1295 (1991)).

Combined administration of ET-1 and ET-1 antibody to rabbits showed significant inhibition of the blood pressure (BP) and renal blood flow responses (Miyamori I., et al., "Systemic and Regional Effects of Endothelin in Rabbits: Effects of Endothelin Antibody," *Clin. Exp. Pharmacol. Physiol.*, 17:691 (1990)).

Other investigators have reported that infusion of ET-specific antibodies into spontaneously hypertensive rats (SHR) decreased mean arterial pressure (MAP), and increased glomerular filtration rate and renal blood flow. In the control study with normotensive Wistar-Kyoto rats (WKY) there were no significant changes in these parameters (Ohno A., "Effects of Endothelin-Specific Antibodies and Endothelin in Spontaneously Hypertensive Rats," *J. Tokyo Women's Med. Coll.*, 61:951 (1991)).

In addition, elevated levels of endothelin have been reported in several disease states (see Table I below).

Burnett and co-workers recently demonstrated that exogenous infusion of ET (2.5 ng/kg/mL) to anesthetized dogs, producing a doubling of the circulating concentration, did have biological actions (Lerman A., et al., "Endothelin has Biological Actions at Pathophysiological Concentrations," *Circulation*, 83:1808 (1991)). Thus heart rate and cardiac output decreased in association with increased renal and systemic vascular resistances and antinatriuresis. These studies support a role for endothelin in the regulation of cardiovascular, renal, and endocrine function.

TABLE I

Plasma Concentrations of ET-1 in Humans

| Condition | Normal Control | ET Plasma Levels Reported (pg/mL) |
|---|---|---|
| Atherosclerosis | 1.4 | 3.2 pmol/L |
| Surgical operation | 1.5 | 7.3 |
| Buerger's disease | 1.6 | 4.8 |
| Takayasu's arteritis | 1.6 | 5.3 |
| Cardiogenic shock | 0.3 | 3.7 |
| Congestive heart failure (CHF) | 9.7 | 20.4 |
| Mild CHF | 7.1 | 11.1 |
| Severe CHF | 7.1 | 13.8 |
| Dilated cardiomyopathy | 1.6 | 7.1 |
| Preeclampsia | 10.4 pmol/L | 22.6 pmol/L |
| Pulmonary hypertension | 1.45 | 3.5 |
| Acute myocardial infarction | 1.5 | 3.3 |
| (several reports) | 6.0 | 11.0 |
|  | 0.76 | 4.95 |
|  | 0.50 | 3.8 |
| Subarachnoid hemorrhage | 0.4 | 2.2 |
| Crohn's Disease | 0–24 fmol/mg | 4–64 fmol/mg |
| Ulcerative colitis | 0–24 fmol/mg | 20–50 fmol/mg |
| Cold pressor test | 1.2 | 8.4 |
| Raynaud's phenomenon | 1.7 | 5.3 |
| Raynaud's/hand cooling | 2.8 | 5.0 |
| Hemodialysis | <7 | 10.9 |
| (several reports) | 1.88 | 4.59 |
| Chronic renal failure | 1.88 | 10.1 |
| Acute renal failure | 1.5 | 10.4 |
| Uremia before hemodialysis | 0.96 | 1.49 |
| Uremia after hemodialysis | 0.96 | 2.19 |
| Essential hypertension | 18.5 | 33.9 |
| Sepsis syndrome | 6.1 | 19.9 |
| Postoperative cardiac | 6.1 | 11.9 |
| Inflammatory arthritides | 1.5 | 4.2 |
| Malignant hemangioendothelioma | 4.3 | 16.2 (after removal) |

In congestive heart failure in dogs and humans, a significant 2- to 3-fold elevation of circulating ET levels has been reported (Rodeheffer R. J., et al., "Circulating Plasma Endothelin Correlates With the Severity of Congestive Heart Failure in Humans," *Am. J. Hypertension*, 4:9A (1991)).

The distribution of the two cloned receptor subtypes, termed $ET_A$ and $ET_B$, have been studied extensively (Arai H., et al., *Nature*, 348:730 (1990), Sakurai T., et al., *Nature*, 348:732 (1990)). The $ET_A$, or vascular smooth muscle receptor, is widely distributed in cardiovascular tissues and in certain regions of the brain (Lin H. Y., et al., *Proc. Natl. Acad. Sci.*, 88:3185 (1991)). The $ET_B$ receptor, originally cloned from rat lung, has been found in rat cerebellum and in endothelial cells, although it is not known if the $ET_B$ receptors are the same from these sources. The human ET receptor subtypes have been cloned and expressed (Sakamoto A., et al., *Biochem. Biophys. Res. Chem.*, 178:656 (1991), Hosoda K., et al., *FEBS Lett.*, 287:23 (1991)). The $ET_A$ receptor clearly mediates vasoconstriction and there have been a few reports implicating the $ET_B$ receptor in the initial vasodilatory response to ET (Takayanagi R., et al., *FEBS Lett.*, 282:103 (1991)). However, recent data has shown that the $ET_B$ receptor can also mediate vasoconstriction in some tissue beds (Panek R. L., et al., *Biochem. Biophys. Res. Commun.*, 183(2):566 (1992)).

A recent study showed that selective $ET_B$ agonists caused only vasodilation in the rat aortic ring, possibly through the release of EDRF from the endothelium (ibid). Thus, reported selective $ET_B$ agonists, for example, the linear analog ET[1,3,11,15-Ala] and truncated analogs ET[6-21, 1,3,11,15-Ala], ET[8-21,11,15-Ala], and N-Acetyl-ET [10-21,11,15-Ala] caused vasorelaxation in isolated, endothelium-intact porcine pulmonary arteries (Saeki T., et al., *Biochem. Biophys. Res, Commun.*, 179:286 (1991)). However, some ET analogs are potent vasoconstrictors in the rabbit pulmonary artery, a tissue that appears to possess an $ET_B$, nonselective type of receptor (ibid).

Plasma endothelin-1 levels were dramatically increased in a patient with malignant hemangioendothelioma (Nakagawa K. et al., *Nippon Hifuka Gakkai Zasshi*, 100:1453–1456 (1990)).

The ET receptor antagonist BQ-123 has been shown to block ET-1 induced bronchoconstriction and tracheal smooth muscle contraction in allergic sheep providing evidence for expected efficacy in bronchopulmonary diseases such as asthma (Noguchi, et al., *Am. Rev. Respir. Dis.*, 145(4 Part 2):A858 (1992)).

Circulating endothelin levels are elevated in women with preeclampsia and correlate closely with serum uric acid levels and measures of renal dysfunction. These observations indicate a role for ET in renal constriction in preeclampsia (Clark B. A., et al., *A. J. Obstet. Gynecol.*, 166:962–968 (1992)).

Plasma immunoreactive endothelin-1 concentrations are elevated in patients with sepsis and correlate with the degree of illness and depression of cardiac output (Pittett J., et al., *Ann. Surg.*, 213(3):262 (1991)).

In addition the ET-1 antagonist BQ-123 has been evaluated in a mouse model of endotoxic shock. This $ET_A$ antagonist significantly increased the survival rate in this model (Toshiaki M., et al., 20.12.90. EP 0 436 189 A1).

Endothelin is a potent agonist in the liver eliciting both sustained vasoconstriction of the hepatic vasculature and a significant increase in hepatic glucose output (Gandhi C. B., et al., *Journal of Biological Chemistry*, 265(29):17432 (1990)). In addition increased levels of plasma ET-1 have been observed in microalbuminuric insulin-dependent diabetes mellitus patients indicating a role for ET in endocrine disorders such as diabetes (Collier A., et al., *Diabetes Care*, 15(8):1038 (1992)).

$ET_A$ antagonist receptor blockade has been found to produce an antihypertensive effect in normal to low renin models of hypertension with a time course similar to the inhibition of ET-1 pressor responses (Basil M. K., et al., *J. Hypertension*, 10 (Suppl. 4):S49 (1992)). The endothelins have been shown to be arrhythmogenic, and to have positive chronotropic and inotropic effects, thus ET receptor blockade would be expected to be useful in arrhythmia and other cardiovascular disorders (Han S.-P., et al., *Life Sci*, 46:767 (1990)).

The widespread localization of the endothelins and their receptors in the central nervous system and cerebrovascular circulation has been described (Nikolov R. K., et al., *Drugs of Today*, 28(5):303–310 (1992)). Intracerebroventricular administration of ET-1 in rats has been shown to evoke several behavioral effects. These factors strongly suggest a role for the ETs in neurological disorders. The potent vasoconstrictor action of ETs on isolated cerebral arterioles suggests the importance of these peptides in the regulation of cerebrovascular tone. Increased ET levels have been reported in some CNS disorders, i.e., in the CSF of patients with subarachnoid hemorrhage and in the plasma of women with preeclampsia. Stimulation with ET-3 under conditions of hypoglycemia have been shown to accelerate the development of striatal damage as a result of an influx of extracellular calcium. Circulating or locally produced ET has been suggested to contribute to regulation of brain fluid balance through effects on the choroid plexus and CSF production. ET-1 induced lesion development in a new model of local ischemia in the brain has been described.

Circulating and tissue endothelin immunoreactivity is increased more than twofold in patients with advanced atherosclerosis (Lerman A., et al., *New England. J. Med.*, 325:997–1001 (1991)). Increased endothelin immunoreactivity has also been associated with Buerger's disease (Kanno K., et al., *J. Amer. Med. Assoc.*, 264:2868 (1990)) and Raynaud's phenomenon (Zamora M. R., et al., *Lancet*, 336:1144–1147 (1990)).

An increase of circulating endothelin levels was observed in patients that underwent percutaneous transluminal coronary angioplasty (PTCA) (Tahara A., et al., *Metab. Clin. Exp.*, 40:1235–1237 (1991)).

Increased plasma levels of endothelin have been measured in rats and humans (Stewart D. J., et al., *Ann. Internal Medicine*, 114:464–469 (1991)) with pulmonary hypertension.

Elevated levels of endothelin have also been measured in patients suffering from ischemic heart disease (Yasuda M., et al., *Amer. Heart J.*, 119:801–806 (1990)) and either stable or unstable angina (Stewart J. T., et al., *Br. Heart J.*, 66:7–9 (1991)).

Infusion of an endothelin antibody 1 hour prior to and 1 hour after a 60 minute period of renal ischaemia resulted in changes in renal function versus control. In addition, an increase in glomerular platelet-activating factor was attributed to endothelin (Lopez-Farre A., et al., *J. Physiology*, 444:513–522 (1991)). In patients with chronic renal failure as well as in patients on regular hemodialysis treatment mean plasma endothelin levels were significantly increased (Stockenhuber F., et al., *Clin. Sci. (Lond.)*, 82:255–258 (1992)).

Local intra-arterial administration of endothelin has been shown to induce small intestinal mucosal damage in rats in a dose-dependent manner (Mirua S., et al., *Digestion*, 48:163–172 (1991)). Furthermore, it has been shown that an anti-ET-1 antibody reduced ethanol-induced vasoconstriction in a concentration-dependent manner (Masuda E., etal., *Am. J. Physiol.*, 262: G785–G790 (1992)). Elevated endothelin levels have been observed in patients suffering from Crohn's disease and ulcerative colitis (Murch S. H., etal., *Lancet*, 339:381–384 (1992)).

The role of endothelins (ET-1, -2, -3) in various physiological and pathophysiological conditions has been studied extensively (Doherty A. D., Endothelin: A New Challenge, *J. Med, Chem,*, 35:1493 (1992); Simonson M. S., Endothelins: Multifunctional Renal Peptides, *Physiological Reviews*, 73:375 (1993)). These peptides act via their receptors viz. $ET_A$ and $ET_B$, which have been cloned and expressed. $ET_A$ specific antagonists have been identified viz. BQ123 (Ishikawa K.; Fukami T., etal., Cyclic pentapeptide endothelin antagonists with high $ET_A$ selectivity, Potency- and solubility-enhancing modifications, *J. Med. Chem.*, 32:2139 (1992); Kiyofumi I., etal., Endothelin antagonistic cyclic pentapeptides. EPA 0436 189 A1 published Jul. 10, 1991), BMS182874 (Stein P. D., et al., Sulfonamide endothelin antagonists.

EP 0558258 A1, published Sep. 1, 1993) and FR 139317 (Keiji H., et al., Peptides having endothelin antagonist activity, a process for the preparation thereof and pharmaceutical compositions comprising the same. EP 0457195 A2, published Nov. 21, 1991). Several non-selective $ET_A/ET_B$ antagonists have also been identified including PD 142893 (Cody W. L., etal., Design of a functional hexapeptide antagonist of endothelin, *J. Med. Chem.*, 35:3301 (1992); Doherty A.M., et al., Structure-activity relationships of C-terminal endothelin hexapeptide antagonists, *J. Med,. Chem.*, 26:2585 (1993)), PD 145065 (Cody W. L., et al., The rational design of a highly potent combined $ET_A$ and $ET_B$ receptor antagonist (PD 145065) and related analogues, *Med. Chem, Res.*, 3:154 (1993); Doherty A. M., et al., In vitro and in vivo studies with a series of hexapeptide endothelin antagonists, *J. Cardiovasc. Pharmacol.* 1, 1993, in press), Ro 46-2005 (Burri K., et al., Application of sulfonamides as therapeutics and new sulfonamides. EP 0510526 A1, published Oct. 28, 1992; Clozel M., et al., The discovery of Ro 46-2005, an orally available non-peptide antagonist of $ET_A$ and $ET_B$ receptors. 3rd International Endothelin Symposium, Houston, Tex., February 1993; Clozel M., et al., Pathophysiological role of endothelin revealed by the first orally active endothelin receptor antagonist, *Nature*, 365:759 (1993)), and Ro 47-0203 (Roux S. P., et al., Ro 47-0203, a new endothelin receptor antagonist reverses chronic vasospasm in experimental subarachnoid hemorrhage, *Circulation*, 4(Part 2, Supplement):I-170 (1993)). These antagonists have blocked the vasoconstrictive effects of ET peptides in several in vivo disease models.

For example, BQ123 has been effective in antagonizing the ET-1 induced pressor response in conscious rats (Ihara M., et al., In vitro biological profile of highly potent novel endothelin (ET) antagonist BQ-123 selective for the $ET_A$ receptor, *J. Cardiovasc. Pharmacol.*, 20(S12):S11 (1992); Ihara M., et al., Biological profiles of highly potent novel endothelin antagonists selective for the $ET_A$ receptor, *Life Sci.*, 50:247 (1992)). Intravenous infusion of BQ123 decreased blood pressure significantly in stroke prone spontaneous hypertensive rats and was effective in the prevention of acute hypoxia induced pulmonary hypertension (McMahon E. G., et al., Effect of phosphoramidon (endothelin converting enzyme inhibitor) and BQ-123 (Endothelin receptor subtype-A antagonist) on blood pressure in hypertensive rats, *Am. J. Hypertension*, 6:667 (1993)). ET-1 induced vasoconstriction in rabbit retinal arteries and the renal vascular resistance in rats was blocked by i.v. BQ123 (Takei K., etal., Analysis of vasocontractile response to endothelin-1 in rabbit retinal vessels using an $ET_A$ receptor antagonist and an $ET_B$ receptor agonist, *Life Sci.*, 53: PL111 (1993)). Cyclosporine A (CsA) induced ET-1 release in vivo (Fogo A., et al., Severe endothelial injury in a renal transplant patient receiving cyclosporine, *Transplantation*, 49:1190 (1990); Watschinger B., et al., Cyclosporine A toxicity is associated with reduced endothelin immunoreactivity in renal endothelium, *Transplant. Proc.*, 24:2618 (1992); Awazu M., etal., Cyclosporine promotes glomerular endothelin binding in vivo, *J. Am. Soc. Nephrol.*, 1;1253 (1991); Bloom I. T., etal., Acute cyclosporine-induced renal vasoconstriction is mediated by endothelin-1, *Surgery*, 114:480 (1993)), which caused renal vasoconstriction (Kon V. and Awazu M., Endothelin and cyclosporine nephrotoxicity, *Renal Fall.*, 14:345 (1992); Brooks D. P., etal., Effect of nifedipine on cyclosporine A-induced nephrotoxicity, urinary endothelin excretion and renal endothelin receptor number, *Eur. J. Pharmacol.*, 194:115 (1991)). This acute CsA toxicity was suppressed by BQ123 in a rat model (Fogo A., etal., Endothelin receptor antagonism is protective in in vivo acute cyclosporin toxicity, *Kidney Int.*, 4.2:770 (1992)). BQ123 (i.v.) prevents the mitochondrial $[Ca^{2+}]$ accumulation in the early phase of ischemic acute renal failure in rats and protects proximal tubular cells from post-ischemic degeneration suggesting possible involvement of endothelin in the pathogenesis of tubular cell injury in the acute ischemic renal failure model (Mino N., et al., Protective effect of a selective endothelin receptor antagonist, BQ-123, in ischemic acute renal failure in rats, *Eur. J. Pharmacol.*, 221:77 (1992)).

Intraperitoneal administration of FR 139317 in rats reduced abnormal permeability to proteins and limited glomerular injury and prevented renal function deterioration. Intracisternal administration of FR 139317 significantly reduced the vasoconstriction of the basilar artery in canine subarachnoid hemorrhage model (Nirei H., et al., An endothelin $ET_A$ receptor antagonist FR 139317 ameliorates cerebral vasospasm in dogs, *Life Sci.*, 5:1869 (1993)). ET-1 induced arrhythmia in rats (Sogabe K., et al., Pharmacological profile of FR 139317, a novel, potent endothelin $ET_A$ receptor antagonist, *J. PharmaCO1. Exp. Ther.*, 264:1040 (1993)) was also suppressed by FR 139317.

Non-selective $ET_A/ET_B$ antagonists like PD 145065 and PD 142893 antagonized both pressor and depressor responses induced by ET-1 in a dose-dependent manner in anesthetized ganglionic blocked rats (Doherty A. M., et al., In vitro and in vivo studies with a series of hexapeptide endothelin antagonists, *J. Cardiovasc. Pharmacol.*, 1993, in press). ET-1 induced reductions in renal flow in anesthetized rats (Wellings R. P., et al., Vasoconstriction in the rat kidney induced by endothelin-1 is blocked by PD 145065, Third International Conference on Endothelin, Houston, Feb. 15–17, 1993, Abstract 139) was completely inhibited by prior administration of PD 145065. In anesthetized guinea pig PD 145065 blocked the increase in pulmonary insufflation pressure induced by ET-1 (Warner T. D., et al., Inhibition by a non-selective endothelin receptor antagonist of bronchoconstrictions induced by endothelin-1 or sarafotoxin 6c in the anesthetized guinea pig, *Br. J, Pharmacol.* in press). Ro 46-2005 demonstrated a protective effect for renal vasoconstriction after renal ischemia in anesthetized rats and also dramatically reduced cerebral vasoconstriction after subarachnoid hemorrhage in rats. Orally administered Ro 46-2005 showed marked antihypertensive effect with a reasonably long duration (Clozel M., et al., The discovery of Ro 46-2005, an orally available non-peptide antagonist of $ET_A$ and $ET_B$ receptors, Third International Endothelin Symposium, Houston, Tex., February 1993; Clozel M., et al., Pathophysiological role of endothelin revealed by the first orally active endothelin receptor antagonist, *Nature*, 365:759 (1993)). Ro 47-0203 was effective in a rabbit subarachnoid hemorrhage model in reversing vasoconstriction indicating that this compound crosses the blood brain barrier (Roux S. P., et al., Ro 47-0203, a new endothelin receptor antagonist reverses chronic vasospasm in experimental subarachnoid hemorrhage, *Circulation*, 4(Part 2, Supplement):I-170 (1993)). Ro 47-203 is reported to be in early clinical trials for SAH and hypertension (Roux S. P., et al., Ro 47-0203, a new endothelin receptor antagonist reverses chronic vasospasm in experimental subarachnoid hemorrhage, *Circulation*, 4(Part 2, Supplement):I-170 (1993)).

Recently at the 3rd International Conference on Endothelin, Houston, Tex., February 1993, the nonpeptide endothelin antagonist RO 46-2005 has been reported to be effective in models of acute renal ischemia and subarachnoid hemorrhage in rats (Clozel M., et al., "Pathophysiological role of endothelin revealed by the first orally active endothelin receptor antagonist," *Nature*, 365:759 (1993)). In addition, the ETA antagonist BQ-123 has been shown to prevent early cerebral vasospasm following subarachnoid hemorrhage (Clozel, M. and Watanabe H., *Life Sci.*, 52:825–834 (1993)).

Most recently an $ET_A$ selective antagonist demonstrated an oral antihypertensive effect (Stein P. D., et al., "The Discovery of Sulfonamide Endothelin Antagonists and the Development of the Orally Active $ET_A$ Antagonist 5-(Dimethylamino)-N-(3,4-dimethyl-5-isoxazolyl)-1-naphthalenesulfonamide," *J. Med. Chem.*, 37:329–331 (1994)).

Elevated levels of endothelin have been postulated to be involved in a number of pathophysiological states including diseases associated with the cardiovascular system as well as various metabolic and endocrinological disorders. As antagonists of endothelin, the compounds of Formula I are useful in the treatment of hypertension, myocardial infarction, diabetes, cerebral vasospasm, cirrhosis, septic shock, congestive heart failure, endotoxic shock, subarachnoid hemorrhage, arrhythmias, asthma, chronic and acute renal failure, preeclampsia, atherosclerotic disorders including Raynaud's disease and restenosis, angina, cancer, pulmonary hypertension, ischemic disease, gastric mucosal damage, hemorrhagic shock, ischemic bowel disease, head injury, and stroke.

A still further embodiment of the present invention is a pharmaceutical composition for administering a therapeutically effective amount of a compound of Formula I in unit dosage form in the treatment methods mentioned above.

Finally, the present invention is directed to methods for production of a compound of Formula I.

SUMMARY

The instant invention relates to novel acylated amino acids that have endothelin antagonist activity. They are compounds of formula

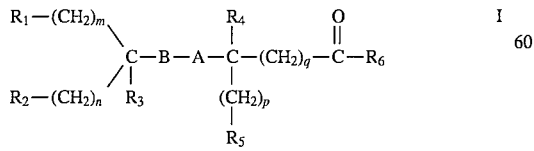

or a pharmaceutically acceptable salt thereof wherein $R_1$ and $R_2$ are each independently a substituted or unsubstituted aryl, partially or completely saturated compound derived from the aryl, or heteroaryl, or partially or completely saturated compound derived from the heteroaryl, or is a substituted or unsubstituted 3- to 5-membered cycloalkyl;

m and n are each independently an integer of from 1 to 3;

$R_3$ is hydrogen or a straight or branched alkyl of from 1 to 4 carbon atoms;

B is absent or —CH═CH—, or —(CH$_2$)$_r$ wherein r is an integer of from 1 to 3;

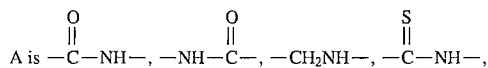

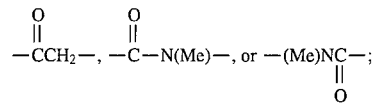

$R_4$ is a straight or branched alkyl of from 1 to 4 carbon atoms, alkenyl of from 2 to 4 carbon atoms, or benzyl or benzyl substituted with 1 to 3 halo, alkoxy, or alkyl groups;

p is an integer of from 0 to 3;

$R_5$ is a substituted or unsubstituted aryl, partially or completely saturated compound derived from the aryl, or a heteroaryl group, or partially or completely saturated compound derived from the heteroaryl;

q is an integer of from 0 to 3; and $R_6$ is $OR_7$ wherein $R_7$ is hydrogen or lower alkyl or $R_6$ is $NR_8R_9$, wherein $R_8$ and $R_9$ are each independently hydrogen or lower alkyl; or $R_8$ and $R_9$ together form a ring of from 3 to 7 atoms selected from carbon, nitrogen, sulfur, and oxygen wherein the ring may not contain more than 2 heteroatoms, and the heteroatoms must be separated by 2 carbons.

Preferred compounds of the invention are those of Formula I above wherein $R_1$ and $R_2$ are each independently a substituted or unsubstituted phenyl or naphthyl, or a phenyl or naphthyl which is partially or completely saturated;

m and n are each independently an integer of from 1 to 2;

$R_3$ is hydrogen or methyl;

B is absent;

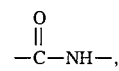

A is —C—NH—, or —CH$_2$NH—;

$R_4$ is a straight or branched alkyl of from 1 to 4 carbon atoms, alkenyl of from 2 to 4 carbon atoms, or benzyl;

p is an integer of from 1 to 2;

$R_5$ is a substituted or unsubstituted aryl, or a partially or completely saturated compound derived from the aryl, or heteroaryl group, or a partially or completely saturated compound derived from the heteroaryl;

q is an integer of from 0 to 1;

$R_6$ is $OR_7$ or $NR_8R_9$ wherein $R_7$ is hydrogen, $R_8$ and $R_9$ are each independently hydrogen or lower alkyl; or $R_8$ and $R_9$ together form a ring of from 5 to 7 atoms selected from carbon, nitrogen, and oxygen, wherein the ring may not contain more than 2 heteroatoms, and the heteroatoms must be separated by 2 carbons.

More preferred compounds of the invention are those of Formula I above wherein

R$_1$ and R$_2$ are each independently selected from phenyl, naphthyl, 3,4-methylenedioxyphenyl, 2,3-dimethylphenyl, 5,6,7,8-tetrahydro-1-naphthyl, 2,3,4,5,6-pentafluorophenyl, 2-methylphenyl, 3-methylphenyl, and cyclohexyl;

m and n are each independently an integer of from 1 to 2;

R$_3$ is hydrogen;

B is absent;

A is 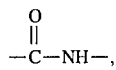, or —CH$_2$NH—;

R$_4$ is methyl;

p is 1;

R$_5$ is indole, phenyl, naphthyl, 4-hydroxyphenyl;

q is an integer of from 0 to 1; and

R$_6$ is OH, NH$_2$, N (CH$_3$)$_2$, or N 

Still more preferred are:

Bis-(1-naphthylmethyl)acetyl-(α-methyl-D-tryptophan);

Bis-(3,4-methylenedioxyphenylmethyl)acetyl-(α-methyl-D-tryptophan);

Bis-(2-naphthylmethyl)acetyl-(α-methyl-D-tryptophan);

Bis-(2,3-dimethylphenylmethyl)acetyl-(α-methyl-D-tryptophan);

Bis-(5,6,7,8-tetrahydro-1-naphthylmethyl)-acetyl-(α-methyl-D-tryptophan);

Bis-(2,3,4,5,6-pentafluorophenylmethyl)-acetyl-(α-methyl-D-tryptophan);

Bis-(1-naphthylmethyl)acetyl-(α-methyl-L-tryptophan);

2-(1-Naphthylmethyl)-2-benzylacetyl-(α-methyl-D-tryptophan);

Bis-(2-methylphenylmethyl)acetyl-(α-methyl-D-tryptophan);

Bis-(3-methylphenylmethyl)acetyl-(α-methyl-D-tryptophan);

Bis-2-(1-naphthylmethyl)-2-methylacetyl-(α-methyl-D-tryptophan);

Bis-(1-naphthylmethyl)acetyl-(α-methyl-D,L-phenylalanine);

Bis-(1-naphthylmethyl)acetyl-(α-methyl-D,L- tyrosine);

N-[2-bis-(1-naphthylmethyl)ethyl]-(α-methyl-D-tryptophan); and

Bis-(cyclohexylmethyl)acetyl-(α-methyl-D-tryptophan).

The invention includes pharmaceutical compositions and methods of using the compounds of the invention. The compounds are useful in treating elevated levels of endothelin, acute and chronic renal failure, hypertension, myocardial infarction and myocardial ischemia, cerebral vasospasm, cirrhosis, septic shock, congestive heart failure, endotoxic shock, subarachnoid hemorrhage, arrhythmias, asthma, preeclampsia, atherosclerotic disorders including Raynaud's disease and restenosis, angina, cancer, pulmonary hypertension, ischemic disease, gastric mucosal damage, hemorrhagic shock, ischemic bowel disease, diabetes, head injury, and stroke.

DETAILED DESCRIPTION

In the compounds of the invention, the term "aryl" means an aromatic group selected from phenyl, naphthyl, anthracenyl, fluorenyl, and the like, unsubstituted or substituted by from 1 to 3 substituents selected from alkyl, alkoxy, hydroxy, or halogen. Partially or completely saturated compounds derived from the aryl groups are also included.

Preferred aryl groups are phenyl, naphthyl, 3,4-methylenedioxyphenyl, 2,3-dimethylphenyl, 5,6,7,8-tetrahydro-1-naphthyl, 2,3,4,5,6-pentafluorophenyl, 2-methylphenyl, 3-methylphenyl, and cyclohexyl which is a completely saturated phenyl.

The term "heteroaryl" means a heteroaromatic group which is 2- or 3-thienyl, 2- or 3-furanyl, 2- or 3-pyrrolyl, 2-, 4-, or 5-imidazolyl, 3-, 4-, or 5-pyrazolyl, 2-, 4-, or 5-thiazolyl, 3-, 4-, or 5-isothiazolyl, 2-, 4-, or 5-oxazolyl, 3-, 4-, or 5-isoxazolyl, 3- or 5-1,2,4-triazolyl, 4- or 5-1,2,3-triazolyl, tetrazolyl, 2-, 3-, or 4-pyridinyl, 3-, 4-, or 5-pyridazinyl, 2-pyrazinyl, 2-, 4-, or 5-pyrimidinyl, 2-, 3-, 4-, 5-, 6-, 7-, or 8-quinolinyl, 1-, 3-, 4-, 5-, 6-, 7-, or 8-isoquinolinyl, 2-, 3-, 4-, 5-, 6-, or 7-indolyl, 2-, 3-, 4-, 5-, 6-, or 7-benzo[b]thienyl, or 2-, 4-, 5-, 6-, or 7-benzoxazolyl, 2-, 4-, 5-, 6-, or 7-benzimidazolyl, 2-, 4-, 5-, 6-, or 7-benzothiazolyl, unsubstituted or substituted by 1 to 3 substituents selected from alkyl, hydroxy, or halogen. Partially or completely saturated compounds derived from the heteroaryl groups are also included, for example, perhydroindole.

Preferred heteroaryls are 3-indole, pyridine, and quinoline.

"Halogen" is fluorine, chlorine, bromine or iodine. Preferred are fluorine and chlorine.

The term "cycloalkyl" means a saturated hydrocarbon ring which contains from 3 to 7 carbon atoms unless otherwise specified, for example, cyclopropyl, cyclobutyl, cyclopentyl, and cycloheptyl. The cycloalkyl ring may be unsubstituted or substituted by from 1 to 3 substituents selected from alkyl, alkoxy, hydroxy, or halogen.

The preferred cycloalkyl is cyclopentyl.

Alkyl is a straight or branched carbon chain of from 1 to 6 atoms unless otherwise specified. Preferred are methyl, ethyl, propyl, and isobutyl.

Alkenyl is a straight or branched carbon chain of from 2 to 6 carbons. Preferred are allyl, vinyl, 2-methylallyl, and butenyl.

R$_8$ and R$_9$, together with the nitrogen to which they are attached, may form a ring of from 3 to 7 atoms. Heteroatoms in the ring are selected from nitrogen, oxygen, and sulfur. Preferred are nitrogen and oxygen wherein the ring may not contain more than 2 heteroatoms and the heteroatoms must be separated by 2 carbon atoms. Preferred groups are pyrrolidine, piperidine, morpholine, and N-methylpiperazine.

Some of the compounds of Formula I are capable of further forming both pharmaceutically acceptable acid addition and/or base salts. All of these forms are within the scope of the present invention.

Pharmaceutically acceptable acid addition salts of the compounds of Formula I include salts derived from nontoxic inorganic acids such as hydrochloric, nitric, phosphoric, sulfuric, hydrobromic, hydriodic, hydrofluoric, and the like, as well as the salts derived from nontoxic organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, trifluoroacetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, galacturonate (see, for example, Berge S.M., et al., "Pharmaceutical Salts," *Journal of pharmaceutical Science,* 66:1–19 (1977)).

The acid addition salts of said basic compounds are prepared by contacting the free base form with a sufficient amount of the desired acid to produce the salt in the conventional manner.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are ammonia, methylamine, dimethylamine, ethylamine, N,N'-dibenzylethylenediamine, chloroprocaine, choline, diethanolamine, dicyclohexylamine, ethylenediamine, N-methylglucamine, and procaine (see, for example, Berge S. M., supra., 1977).

The base addition salts of said acidic compounds are prepared by contacting the free acid form with a sufficient amount of the desired base to produce the salt in the conventional manner.

Certain of the compounds of the present invention can exist in unsolvated forms as well as solvated forms, including hydrated forms. In general, the forms, including hydrated forms, are equivalent to unsolvated forms and are intended to be encompassed within the scope of the present invention.

Certain of the compounds of the present invention possess one or more chiral centers and each center may exist in the R(D) or S(L) configuration. The present invention includes all enantiomeric and epimeric forms as well as the appropriate mixtures thereof. The following schemes illustrate the processes of the invention.

SCHEME 1
Example 1

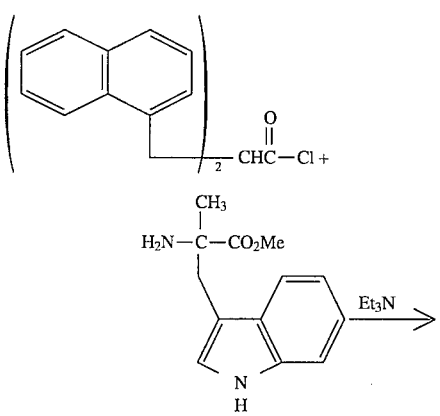

SCHEME 1
Example 1

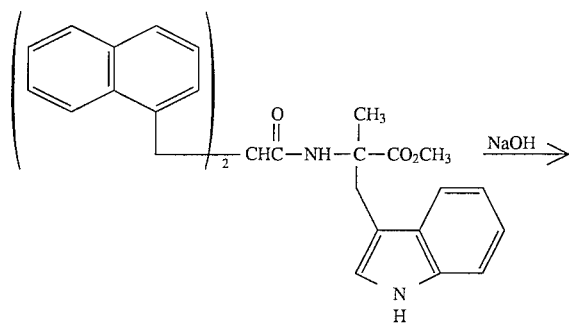

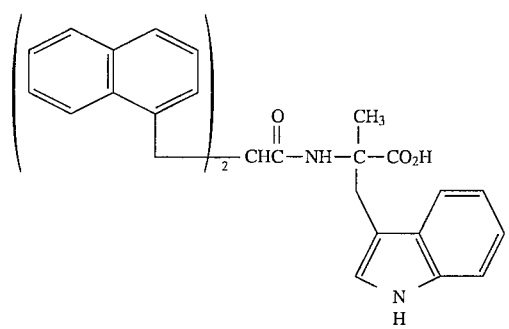

SCHEME 2
Example 2

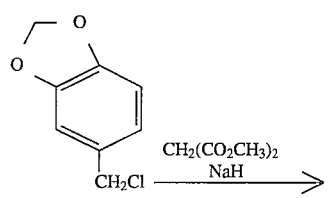

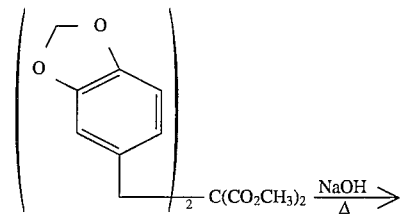

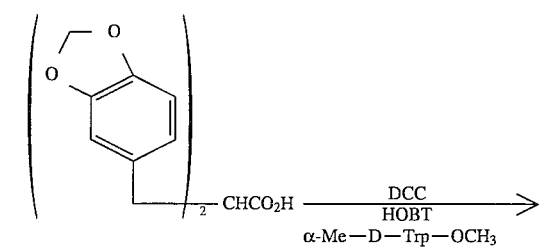

SCHEME 2
Example 2

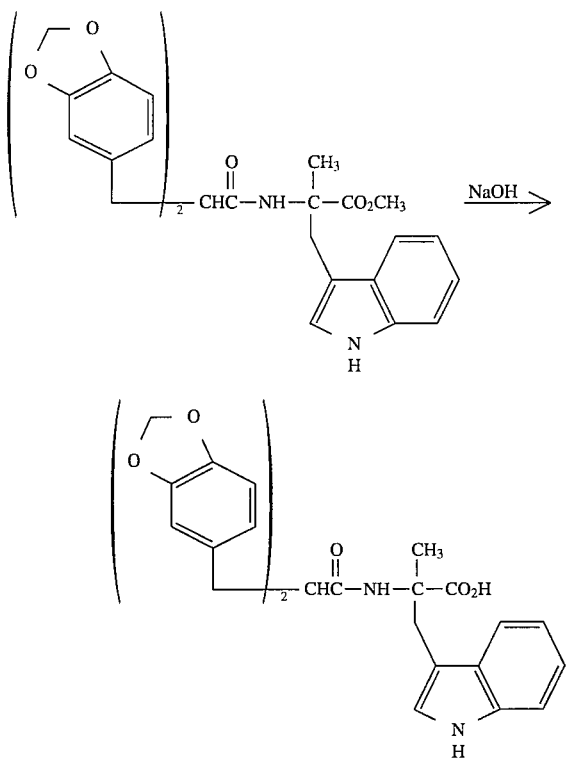

The compounds of Formula I are valuable antagonists of endothelin. The tests employed here indicate that compounds of the invention possess endothelin antagonist activity. The compounds were tested for their ability to inhibit [$^{125}$I]-ET-1([$^{125}$I]-Endothelin-1) binding in a receptor assay. The following testing procedures were used (Doherty A.M., et al., "Design of C-Terminal Peptide Antagonists of Endothelin: Structure-Activity Relationships of ET-1 [16–21, D-His$^{16}$]", *Bioorganic and Medicinal Chemistry Letters*, 3:497–502 (1993)).

ENDOTHELIN RECEPTOR BINDING ASSAY-A (EREA-A) INTACT CELL BINDING OF [$^{125}$I]-ET-1

Materials and Terms Used:
Cells

The cells used were rabbit renal artery vascular smooth muscle cells grown in a 48-well dish (1 cm$^2$) (confluent cells).
Growth Media The growth media was Dulbecco's Modified Eagles/Ham's F12 which contained 10% fetal bovine serum and antibiotics (penicillin/streptomycin/fungizone)Assay
Assay Buffer The assay buffer was a medium 199 containing Hanks salts and 25 mM Hepes buffer (Gibco 380-2350AJ), supplemented with penicillin/streptomycin/fungizone (0.5%) and bovine serum albumin (1 mg/mL).
[$^{125}$I]-ET-1

Amersham radioiodinated endothelin-1[$^{125}$I]-ET-1 was used at final concentration of 20,000 cpm/0.25 mL (25 pM).
Protocol First, add 0.5 mL warm assay buffer (described above) to the aspirated growth media and preincubate for 2 to 3 hours in a 37° C. water bath (do not put back in the 5% carbon dioxide). Second, remove the assay buffers, place the dish on ice, and add 150 µL of cold assay buffer described above to each well. Third, add 50 mL each of cold [$^{125}$I]-ET-1 and competing ligand to the solution (at the same time if possible). Next, place dish in a 37° C. water bath for about 2 hours and gently agitate the dish every 15 minutes. Discard the radioactive incubation mixture and wash wells 3 times with 1 mL of cold phosphate buffered saline. Last, add 250 mL of 0.25 molar sodium hydroxide, agitate for 1 hour on a rotator, and then transfer the sodium hydroxide extract to gamma counting tubes and count the radioactivity.

ENDOTHELIN RECEPTOR BINDING ASSAY-B (EREA-B) [$^{125}$I]-ET-1 BINDING IN RAT CEREBELLAR MEMBRANES

Materials and Terms Used:
Tissue Buffer

The tissue is made up of 20 mM tris(hydroxymethyl)aminomethane hydrochloride (Trizma) buffer, 2 mM ethylenediaminetetraacetate, 100 µM phenylmethylsulfonyl fluoride.
Tissue Preparation First, thaw one aliquot of frozen rat cerebellar membranes (2 mg protein in 0.5 mL). Next, add 0.5 mL membrane aliquot to 4.5 mL cold tissue buffer, polytron at 7,500 revolutions per minute for 10 seconds. Finally, dilute tissue suspension 1/100 (0.1 mL suspension+9.9 mL tissue buffer), polytron again, and place ice.
Dilution Buffer Medium 199 with Hank's salts plus 25 mM Hepes+1 mg/mL bovine serum albumin.
[$^{125}$I]-ET-1

Amersham [$^{125}$I]-ET-1 (aliquots of 2×10$^6$ cpm per 100 mL aliquot of [$^{125}$I]-ET-1 with 5.2 mL dilution buffer, place on ice until use (final concentration will be 20,000 cpm per tube, or 25 pM).
Protocol Add 50 µL each of cold [$^{125}$]-ET-1 and competing ligand to tubes on ice. Mix in 150 µL of tissue to each tube, vortex briefly, then tap to force all liquids to bottom (total assay volume=250 µL). Then place the tubes in a 37° C. water bath for 2 hours.

Add 2.5 mL cold wash buffer (50 mM Trizma buffer) to each tube, filter, and then wash tube with additional 2.5 mL wash buffer and add to filter. Finally, wash filters with an additional 2.5 mL of cold wash buffer.

Count filters for radioactivity in gamma counter.

The above process has also been modified by using human recombinant CHO-K1 cells.

The tissue used for human ETB (HERBA-B assay) was recombinant human ETB receptor expressed in CHO-K1 cells (Chinese hamster ovary cells). The gene for human ETB receptor was cloned and inserted into the pRc-CMW expression vector, then transfected into CHO-K1 cells by electroporation. For binding assays, membranes (0.7 mg protein) of CHO-K1 cells expressing recombinant human ETB receptor were used.

IN VITRO INHIBITION OF ET-3 STIMULATED ARACHIDONIC ACID RELEASE (AAR) IN CULTURED CHINESE HAMSTER OVARY (CHO) CELLS EXPRESSING RECOMBINANT ET$_B$ RECEPTORS BY THE COMPOUNDS OF THE INVENTION

Antagonist activity is measured by the ability of added compounds to reduce endothelin-stimulated arachidonic acid release in cultured Chinese hamster ovary (CHO) cells expressing recombinant $ET_B$ receptors as arachidonic acid release (AAR). [$^3$H]Arachidonic Acid Loading Media (LM) is DME/F12+0.5% FCS×0.25 mCi/mL [3H]arachidonic acid (Amersham). Confluent monolayers of cultured Chinese hamster ovary cells (CHO) expressing recombinant $ET_B$ receptors were incubated in 0.5 mL of the LM over 5 hours, at 37° C., in 5% $CO_2$. The LM was aspirated and the cells were washed twice with the assay buffer (Hank's BSS+10 mM HEPES+fatty acid-free BSA (1 mg/mL)), and incubated for 15 minutes with 1 mL of the prewarmed assay buffer. The same procedure was repeated with the inclusion of assay buffer containing 100 μg/mL of unlabelled arachidonic acid and 10 μL of the test compound (1 nM to 1 μM) and 10 μL ET-3 (1.0 nM), and the incubation was continued for 10 minutes. This solution was then collected, 10 mL of scintillation cocktail was added, and the amount of [$^3$H]arachidonic acid was determined in a liquid scintillation counter.

TABLE 1

| | $IC_{50}$ in μM | | | |
|---|---|---|---|---|
| Example | ERBA-A | ERBA-B | HERBA-B | AAR-B (Antagonist) |
| 1 | 10 | 0.6 | 0.57 | 2.5 |
| 2 | >25 | | 1.6 | |
| 3 | >25 | | 16 | |
| 4 | >25 | | 2.9 | |
| 5 | >25 | | 19 | |
| 6 | 14 | | 1.4 | |
| 7 | >25 | | 27 | |
| 8 | >30 | 17 | | |
| 9 | 26 | | 2.2 | 6.6 |
| 10 | >25 | | 1.5 | 9.5 |
| 11 | >25 | | 4.7 | 9.9 |
| 12 | >25 | | 10 | |
| 13 | 14 | | 6.5 | |
| 14 | 25 | | 18 | |
| 15 | 14 | | 9.2 | |
| 16 | >25 | | 7.4 | |

The compounds of the present invention can be prepared and administered in a wide variety of oral and parenteral dosage forms. Thus, the compounds of the present invention can be administered by injection, that is, intravenously, intramuscularly, intracutaneously, subcutaneously, intraduodenally, or intraperitoneally. Also, the compounds of the present invention can be administered by inhalation, for example, intranasally. Additionally, the compounds of the present invention can be administered transdermally. It will be obvious to those skilled in the art that the following dosage forms may comprise as the active component, either a compound of Formula I or a corresponding pharmaceutically acceptable salt of a compound of Formula I.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, binders, preservatives, tablet disintegrating agents, or an encapsulating material.

In powders, the carrier is a finely divided solid which is in a mixture with the finely divided active component.

In tablets, the active component is mixed with the carrier having the necessary binding properties in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogenous mixture is then poured into convenient sized molds, allowed to cool, and thereby to solidify.

Liquid form preparations include solutions, suspensions, and emulsions, for example, water or water propylene glycol solutions. For parenteral injection liquid preparations can be formulated in solution in aqueous polyethylene glycol solution.

Aqueous solutions suitable for oral use can be prepared by dissolving the active component in water and adding suitable colorants, flavors, stabilizing and thickening agents as desired.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsules, tablet, cachet, or lozenge itself, or it can be the appropriate number of any of these in packaged form.

The quantity of active component in a unit dose preparation may be varied or adjusted from 0.1 mg to 100 mg preferably 0.5 mg to 100 mg according to the particular application and the potency of the active component. The composition can, if desired, also contain other compatible therapeutic agents.

In therapeutic use as antagonists of endothelin, the compounds utilized in the pharmaceutical method of this invention are administered at the initial dosage of about 0.01 mg to about 100 mg/kg daily. A daily dose range of about 0.01 mg to about 10 mg/kg is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day, if desired.

The following nonlimiting examples illustrate the preferred methods for preparing the compounds of the invention.

EXAMPLE 1

Bis-(1-naphthylmethyl)acetyl-(α-methyl-D-tryptophan)

a) Methyl bis-(1-naphthylmethyl)acetyl-(α-methyl-D-tryptophan)

A solution of 2.0 g (8.6 mmol) of methyl α-methyl-D-tryptophan in 30 mL THF was treated with 3.09 g (8.6 mmol) of bis-(1-naphthylmethyl)acetyl chloride (*J. Med. Chem.*, 35:1032 (1992)) followed by 1.2 mL (8.6 mmol) of $Et_3N$. After stirring at room temperature for 2 days, the solvent was removed under reduced pressure and the residue taken up in EtOAc and washed with 1HCl, $H_2O$, saturated $NaHCO_3$, and saturated NaCl. Drying over $MgSO_4$ and removal of the solvent under reduced pressure gave 4.77 g of the crude product. Recrystallization from $CH_3CN/H_2O$ gave 4.24 g (88.9% yield) of the product as a cream solid, mp 193°–195° C. The structure was confirmed by NMR and mass spectroscopy.

Analysis calculated for $C_{37}H_{34}N_2O_3$ (MW 554.66): C, 80.12; H, 6.18; N, 5.05. Found: C, 80.15; H, 6.17; N, 4.72.

b) Bis-(1-naphthylmethyl)acetyl-(α-methyl-D-tryptophan)

A solution of 4.24 g (7.6 mmol) of methyl bis-(1-naphthylmethyl)acetyl-(α-methyl-D-tryptophan) in 50 mL MeOH and 50 mL dioxane was treated with a solution of 1.0 g (25 mmol) of NaOH in 10 mL $H_2O$ and the solution left stirring at room temperature for 4 days. The solvent was removed under reduced pressure and the residue mixed with $H_2O$ and acidified to Congo red end point with dilute HCl. The crude product was collected and chromatographed on silica gel, eluting with $CHCl_3$: MeOH (95:5). There was obtained 2.37 g (57.8% yield) of the product as a solid foam. The structure was confirmed by NMR and mass spectroscopy.

Analysis calculated for $C_{36}H_{32}N_2O_3 \cdot 0.9CHCl_3$ (MW 648.08): C, 68.38; H, 5.12; N, 4.32. Found: C, 68.55; H, 5.21; N, 4.24.

EXAMPLE 2

Bis-(3,4-methylenedioxyphenylmethyl)acetyl-(α-methyl-D-tryptophan a) Dimethyl bis-(3,4-methylenedioxyphenylmethyl)-malonate A suspension of 6.6 g (0.165 mol) of NaH.oil (60%) in 200 mL THF was cooled in ice and treated dropwise with 10 g (0.075 mol) of dimethyl malonate. After stirring for 0.5 hour, the solution was treated with a solution of 27.3 g (0.16 mol) of 3,4-methylenedioxybenzyl chloride (50% in $CH_2Cl_2$). After stirring at room temperature overnight, the solution was heated at reflux overnight. The mixture was filtered and the solvent removed under reduced pressure. The residue was taken up in EtOAc and washed with 1N HCl, then saturated NaCl. Drying over $MgSO_4$ and removal of the solvent under reduced pressure gave the crude product. Recrystallization from EtOAc/hexane gave 20.58 g (68.6% yield) of the product as a solid. The structure was confirmed by NMR spectroscopy.

b) Bis-(3,4-methylenedioxyphenylmethyl)acetic acid

A solution of 20.58 g (0.051 mol) of dimethyl bis-(3,4-methylenedioxyphenylmethyl)malonate in 50 mL of n-butanol was treated with a solution of 8.58 g (0.153 mol) of KOH in 50 mL $H_2O$ and heated at reflux overnight. The solvent was removed under reduced pressure and the residue mixed with $H_2O$ and acidified to pH 2 with dilute HCl. The mixture was extracted with EtOAc and the EtOAc washed with saturated NaCl. Drying over $MgSO_4$ and removal of the solvent under reduced pressure left 9.24 g (55% yield) of the product as a solid, mp 191°–193° C. The structure was confirmed by NMR spectroscopy.

c) Methyl bis-(3,4-methylenedioxyphenylmethyl)acetyl-(α-methyl-D-tryptophan)

A solution of 1.0 g (3.0 mmol) of bis-(3,4-methylenedioxyphenylmethyl)acetic acid in 20 mL DMF was treated with 0.68 g (3.3 mmol) of DCC and 0.45 g (3.3 mmol) of HOBt. A solution of 0.73 g (3.15 mmol) of methyl α-methyl-D-tryptophan in 20 mL EtOAc was then added and the solution left stirring for 3 days. The mixture was filtered and the solvent removed under reduced pressure. The residue was taken up in EtOAc and washed with 1N HCl, then saturated NaCl. Drying over $MgSO_4$ and removal of the solvent under reduced pressure left the crude product. Chromatography on silica gel, eluting with a gradient of 10% EtOAc in hexane to 50% EtOAc in hexane gave 0.78 g (48.8% yield) of the product as a white foam. The structure was confirmed by NMR spectroscopy.

d) Bis-(3,4-methylenedioxyphenylmethyl)acetyl-(α-methyl-D-tryptophan)

A solution of 0.36 g (0.66 mmol) of methyl bis-(3,4-methylenedioxyphenylmethyl)acetyl-(α-methyl-D-tryptophan) in 10 mL MeOH and 2 mL THF was treated with a solution of 0.133 g (3.3 mmol) of NaOH in 2 mL $H_2O$ and the solution stirred at room temperature for 2 days. The solvent was removed under reduced pressure and the residue taken up in EtOAc and washed twice with 1N HCl, then saturated NaCl. Drying over $MgSO_4$ and removal of the solvent under reduced pressure gave the product. This was dissolved in $Et_2O$ and the solvent removed under reduced pressure to give 0.28 g (82.3% yield) of the product as an amorphous white solid. The structure was confirmed by NMR and mass spectroscopy.

Analysis calculated for $C_{30}H_{28}N_2O_7 \cdot 0.17H_2O$ (MW 531.66): C, 67.78; H, 5.37; N, 5.27. Found: C, 67.77; H, 5.40; N, 4.97.

EXAMPLE 3

Bis-(2-naphthylmethyl)acetyl-(α-methyl-D-tryptophan)

a) Dimethyl bis-(2-naphthylmethyl)malonate

Following the procedure described in Example 2a, but using 2-bromomethylnaphthalene as the alkylating agent, there was obtained the product as a white solid. The structure was confirmed by NMR spectroscopy.

b) Bis-(2-naphthylmethyl)acetic acid

Following the procedure described in Example 2b, but using the material from Example 3a, there was obtained 2.0 g (80.6% yield) of the product as a white solid, mp 156°–158° C. The structure was confirmed by NMR spectroscopy.

c) Methyl bis-(2-naphthylmethyl)acetyl-(α-methyl-D-tryptophan)

Following the procedure described in Example 2c, but using bis-(2-naphthylmethyl)acetic acid, there was obtained 0.6 g (37.5% yield) of the product as solid foam. The structure was confirmed by NMR spectroscopy.

d) Bis-(2-naphthylmethyl)acetyl-(α-methyl-D-tryptophan)

Following the procedure described in Example 2d, but using the material from Example 3c, there was obtained 0.33 g (55.5% yield) of the product as a white amorphous solid. The structure was confirmed by NMR and mass spectroscopy.

Analysis calculated for $C_{36}H_{32}N_2O_3$ (MW 540.63): C, 79.98; H, 5.97; N, 5.18. Found: C, 79.86; H, 6.04; N, 5.13.

EXAMPLE 4

Bis-(2,3-dimethylphenylmethyl)acetyl-(α-methyl-D-tryptophan)

a) Dimethyl bis-(2,3-dimethylphenylmethyl)malonate

Following the procedure for Example 2a, but using 2,3-dimethylbenzyl bromide as the alkylating agent, there was obtained 4.18 g (60.8% yield) of the product as a yellow oil. The structure was confirmed by NMR spectroscopy.

b) Bis-(2,3-dimethylphenylmethyl)acetic acid

Following the procedure from Example 2b, but using the material from Example 4a, there was obtained 1.13 g (34.8% yield) of the product as a white solid, mp 150°–152° C. The structure was confirmed by NMR spectroscopy.

c) Methyl bis-(2,3.-dimethylphenylmethyl)acetyl-(α-methyl-D-tryptophan)

Following the procedure from Example 2c, but using the material from Example 4b, there was obtained 0.9 g (44.1% yield) of the product as a solid foam. The structure was confirmed by NMR spectroscopy.

d) Bis-(2,3-dimethylphenylmethyl)acetyl-(α-methyl-D-tryptophan)

Following the procedure from Example 2d, but using the material from Example 4c, and using LiOH as the base, there was obtained 0.31 g (66% yield) of the product as an amorphous solid. The structure was confirmed by NMR and mass spectroscopy.

Analysis calculated for $C_{32}H_{36}N_2O_3 \cdot 0.11 C_4H_8O_2 \cdot 0.01 H_2O$ (MW 506.53 ):

C, 76.92; H, 7.34; N, 5.53. Found: C, 76.91; H, 7.36; N, 5.53.

EXAMPLE 5

Di-benzylacetyl-(α-methyl-D-tryptophan)

a) Di-benzylacetyl chloride

To 20 mL of $SOCl_2$ was added in portions 3.14 g (13.1 mmol) of di-benzylacetic acid and the solution stirred at room temperature overnight. The $SOCl_2$ was removed under reduced pressure and the residue taken up in $Et_2O$ and the solvent removed again. There was obtained 3.18 g (94.1% yield) of the product as an oil. The structure was confirmed by NMR spectroscopy.

b) Methyl di-benzylacetyl-(α-methyl-D-tryptophan)

Following the procedure of Example 1a, but using the di-benzylacetyl chloride, there was obtained after chromatography, eluting with $CHCl_3$: EtOAc (95:5), 1.0 g (70.9% yield) of the product as a white foam. The structure was confirmed by NMR and mass spectroscopy.

c) Di-benzylacetyl-(α-methyl-D-tryptophan)

Following the procedure of Example 1b, but using the material from Example 5b, there was obtained 0.96 g (100% yield) of the product as a white foam. The structure was confirmed by NMR and mass spectroscopy.

Analysis calculated for $C_{28}H_{28}N_2O_3 \cdot 0.2 C_4H_8O_2 \cdot 0.2 C_4H_8O_2$ (MW 475.76):

C, 74.72; H, 6.61; N, 5.89. Found: C, 74.32; H, 6.35; N, 5.80.

EXAMPLE 6

Bis-(5,6,7,8-tetrahydro-1-naphthylmethyl)acetyl-(α-methyl-D-tryptophan)

a) 5,6,7,8-Tetrahydro-1-naphthoic acid

A solution of 10.0 9 (0.058 mol) of 1-naphthoic acid in 100 mL HOAc was treated with 0.5 g $PtO_2$ and reduced at 29° C., 50 psi. When the required amount of $H_2$ had been taken up, the mixture was filtered and the solvent removed under reduced pressure. The residue was recrystallized from EtOAc/hexane to give 6.84 g (67% yield) of the product. The structure was confirmed by NMR spectroscopy.

b) 5,6,7,8-Tetrahydro-1-hydroxymethylnaphthalene

A solution of 20 mL (0.019 mol) of 1.0M $LiAlH_4$ in $Et_2O$ was cooled to −78° C. and treated dropwise with a solution of 3.42 g (0.019 mol) of 5,6,7,8-tetrahydro-1-naphthoic acid in 20 mL THF. The solution was allowed to warm to room temperature and stirred overnight. The solution was cooled to 0° C. and decomposed with 40 mL of a 0.43M solution of $KHSO_4$. The mixture was filtered through Celite and washed with EtOAc. The organic phase was washed with 1N HCl and saturated NaCl. Drying over $MgSO_4$ and removal of the solvent under reduced pressure left 3.02 g (98% yield) of the product. The structure was confirmed by NMR spectroscopy.

c) 5,6,7,8-Tetrahydro-1-bromomethylnaphthelene

A solution of 3.0 g (0.0185 mol) of 5,6,7,8-tetrahydro-1-hydroxymethylnaphthalene in 30 mL $Et_2O$ was cooled in ice and treated with 3.65 g (0.0185 mol) of $BaCO_3$ followed by 0.88 mL (0.0093 mol) of $PBr_3$. The mixture was allowed to warm to room temperature and stirred for 3 days. The mixture was filtered and the filtrate diluted with EtOAc and washed with saturated $NaHCO_3$ and saturated NaCl. Drying over $MgSO_4$ and removal of the solvent under reduced pressure gave a yellow oil which crystallized on standing. The structure was confirmed by NMR spectroscopy.

d) Dimethyl bis-(5,6,7,8-tetrahydro-1-naphthyl-methyl)malonate

Following the procedure described in Example 2a, but using the material from Example 6c, there was obtained 3.19 g (100% yield) of the product as a yellow oil. The structure was confirmed by NMR spectroscopy.

e) Bis-(5,6,7,8-tetrahydro-1-naphthylmethyl)acetic acid

Following the procedure from Example 2b, but using the material from Example 6d, there was obtained 0.6 g (22.8% yield) of the product as a white solid. The structure was confirmed by NMR spectroscopy.

f) Methyl bis-(5,6,7,8-tetrahydro-1-naphthylmethyl)-acetyl-(α-methyl-D-tryptophan)

Following the method of Example 2c, but using the material from Example 6e, there was obtained 0.3 g (31.2% yield of the product. The structure was confirmed by NMR spectroscopy.

g) Bis-(5,6,7,8-tetrahydro-1-naphthylmethyl)acetyl-(α-methyl-D-tryptophan)

Following the method of Example 2d, but using the material from Example 6f, and using LiOH as the base, there was obtained 0.25 g ( 86.2% yield) of the product as a white solid. The structure was confirmed by NMR and mass spectroscopy.

Analysis calculated for $C_{36}H_{40}N_2O_3 \cdot 0.27 C_4H_8O_2 \cdot 0.05 H_2O$ (MW 573.43): C, 77.67; H, 7.43; N, 4.89. Found: C, 77.66; H, 7.35; N, 4.74.

EXAMPLE 7

Bis-(2,3,4,5,6-pentafluorophenylmethyl)acetyl-(α-methyl-D-tryptophan)

a) Dimethyl bis-(2,3,4,5,6-pentafluorophenylmethyl)-malonate

Following the procedure in Example 2a, but using pentafluorobenzyl bromide as the alkylating agent, there was obtained 5.2 g (55% yield) of the product as yellow oil. The structure was confirmed by NMR spectroscopy.

b) Bis-(2,3,4,5,6-pentafluorophenylmethyl)acetic acid

Following the procedure in Example 2b, but using the material from Example 7a, there was obtained 2.36 g (51.1% yield) of the product as a white solid after recrystallization from hexane/EtOAc, mp 144°–145° C. The structure was confirmed by NMR spectroscopy.

c) Methyl bis-(2,3,4,5,6-pentafluorophenylmethyl)-acetyl-(α-methyl-D-tryptophan)

Following the procedure in Example 2c, but using the material from Example 7b, there was obtained 0.67 g (44.1% yield) of the product. The structure was confirmed by NMR spectroscopy.

d) Bis-(3,4,5,6,7-pentafluorophenylmethyl)acetyl-(α-methyl-D-tryptophan)

Following the procedure for Example 2d, but using the material from Example 7c, and using LiOH as the base, there was obtained 0.5 g (76.3% yield) of the product as a white solid. Mass spectroscopy showed product and material where a fluorine atom was replaced by a methoxy group. HPLC analysis showed 58% product and 36% of material containing a methoxy group in place of a fluorine atom.

EXAMPLE 8

Bis-(1-naphthylmethyl)acetyl-(α-methyl-L-tryptophan)

a) Methyl bis-(1-naphthylmethyl)acetyl-(α-methyl-L-tryptophan)

Following the procedure described in Example 1a, but using methyl α-methyl-L-tryptophan, there was obtained crude product. Two chromatographies on silica gel, eluting with $CHCl_3$, followed by crystallization from $CH_3CN$ gave 0.72 g (35.1% yield) of pure product as a white solid, mp 195°–197° C. The structure was confirmed by NMR and mass spectroscopy.

b) Bis-(1-naphthylmethyl)acetyl-(α-methyl-L-tryptophan)

Following the procedure described in Example 1b, but using the material from Example 8a, there was obtained on acidifying the reaction mixture 0.382 g (57.9% yield) of the pure product as an amorphous white solid. The structure was confirmed by NMR and mass spectroscopy.

Analysis calculated for $C_{36}H_{32}N_2O_3 \cdot 0.3H_2O$ (MW 546.04): C, 79.18; H, 6.02; N, 5.13. Found: C, 79.00; H, 5.96; N, 4.82.

EXAMPLE 9

2-(1-Naphthylmethyl)-2-benzylacetyl-(α-methyl-D-tryptophan)

a) Di-t-butyl (1-naphthylmethyl)malonate

A suspension of 5.96 g (0.124 mol) of NaH.oil (50%) was washed with THF to remove the oil, then suspended in 450 mL THF. Di-t-butyl malonate (25.4 mL, 0.113 mol) was then added causing a mild exotherm. The solution was heated to reflux for 45 minutes, then cooled to 30° C. A solution of 20.0 g (0.113 mol) of 1-chloromethylnaphthalene in 50 mL THF was then added and the solution heated at reflux for 3 hours, then left stirring overnight. The mixture was filtered and the filtrate removed under reduced pressure. The residue was taken up in EtOAc and washed with 1N citric acid, saturated NaCl, saturated $NaHCO_3$, then saturated NaCl. Drying over $MgSO_4$ and removal of the solvent under reduced pressure left 39.65 g (98.4% yield) of the product as an oil.

b) Di-t-butyl (1-naphthylmethyl)benzylmalonate

A suspension of 2.96 g (0.062 mol) of NaH. oil (50%) was washed with THF to remove the oil, then suspended in 300 mL THF, and then treated with 20.0 g (0.056 mol) of di-t-butyl (1-naphthylmethyl)malonate. The solution was refluxed for 40 minutes, then cooled to room temperature. A solution of 6.8 mL (0.057 mol) of benzyl bromide in 40 mL THF was then added and the mixture heated at reflux for 15 minutes, then left stirring at room temperature overnight. The solvent was removed under reduced pressure and the residue taken up in EtOAc and washed with 1N citric acid, saturated NaCl, saturated $NaHCO_3$, and saturated NaCl. Drying over $MgSO_4$ and removal of the solvent under reduced pressure left 25 g of a yellow oil. Chromatography on silica gel, eluting with hexane:EtOAc (90:10) gave 20.0 g (80% yield) of the product as a clear oil. The structure was confirmed by NMR and mass spectroscopy.

c) 2-(1-Naphthylmethyl)-2-benzylacetic acid

A solution of 20.0 g (0.045 mol) of di-t-butyl (1-naphthylmethyl)benzylmalonate in 350 mL THF was treated repeatedly with HCl gas over a 3-hour period. The solvent was removed under reduced pressure and the residue heated at 2000° C. for 25 minutes. The residue was taken up in $Et_2O$ and extracted with 1N NaOH. The NaOH solution was acidified with dilute HCl and extracted with $Et_2O$. The $Et_2O$ was washed with saturated NaCl, dried over $MgSO_4$, and the solvent removed under reduced pressure leaving 10.78 g (82% yield) of the product as a white solid. The structure was confirmed by NMR and mass spectroscopy.

d) 2-(1-Naphthylmethyl)-2-benzylacetyl chloride

A solution of 1.5 9 (5.2 mmol) of 2-(1-naphthylmethyl)-2-benzylacetic acid in 10 mL $SOCl_2$ was stirred at room temperature overnight. The $SOCl_2$ was removed under reduced pressure, the residue taken up in $Et_2O$, and the solvent again removed under reduced pressure to give 1.6 g (100% yield) of the product as an oil.

e) Methyl 2-(1-naphthylmethy)-2-benzylacetyl-)αmethyl-D-tryptophan)

Following the procedure described in Example 1a, but using the material from Example 9d, gave crude product. Chromatography on silica gel, eluting with a gradient of $CH_2Cl_2$:MeOH (99:1) to $CH_2Cl_2$:MeOH (98:2) gave 2.37 g of partially purified product. Rechromatography gave 1.46 g (55.9% yield) of the product as a solid foam. The structure was confirmed by NMR and mass spectroscopy.

f) 2-(1-Naphthylmethyl)-2-benzylacetyl-(α-methyl-D-tryptophan)

Following the procedure outlined in Example 1b, but using the material from Example 9e, there was obtained 0.528 g (85.2% yield) of the product as a mixture of diastereomers as a white solid. The structure was confirmed by NMR and mass spectroscopy.

Analysis calculated for $C_{32}H_{30}N_2O_3 \cdot H_2O$ (MW 508.59): C, 75.57; H, 6.34; N, 5.51. Found: C, 75.47; H, 5.82; N, 5.39.

EXAMPLE 10

Bis-(2-methylphenylmethyl)acetyl-(α-methyl-D-tryptophan)

a) Bis-(2-methylphenylmethyl)acetic acid

Following the procedure for Examples 2a and 2b, but using 2-methylbenzyl bromide as the alkylating agent, there was obtained the product as a white solid, mp 94°–96° C. The structure was confirmed by NMR and mass spectroscopy.

b) Bis-(2-methylphenylmethyl)acetyl chloride

Following the procedure of Example 9d, but using bis-(2-methylphenylmethyl)acetic acid, there was obtained 3.79 g (100% yield) of the product which was used directly in the following reaction.

c) Methyl bis-(2-methylphenylmethyl)acetyl-(α-methyl-D-tryptophan)

Following the method of Example 1a, but using the material from Example 10b, there was obtained the crude product. Chromatography on silica gel, eluting with hexane:EtOAc (50:50) gave 2.49 g (39.1% yield) of the pure product as a foam. The structure was confirmed by NMR and mass spectroscopy.

d) Bis-(2-methylphenylmethyl)acetyl-(α-methyl-D-tryptophan)

Following the method outlined in Example 1b, but using the material from Example 10c, there was obtained 2.41 g (100% yield) of the product as a white foam. The structure was confirmed by NMR and mass spectroscopy.

EXAMPLE 11

Bis-(3-methylphenylmethyl)acetyl-(α-methyl-D-tryptophan)

a) Bis-(3-methylphenylmethyl)acetic acid

Following the procedure for Examples 2a and 2b, but using 3-methylbenzyl bromide as the alkylating agent, there was obtained the product as a white solid, mp 86°–88° C. The structure was confirmed by NMR and mass spectroscopy.

b) Bis-(3-methylphenylmethyl)acetyl chloride

Following the procedure of Example 9d, but using bis-(3-methylphenylmethyl)acetic acid, there was obtained the product which was used directly in the following reaction.

c) Methyl bis-(3-methylphenylmethyl)acetyl-(α-methyl-D-tryptophan)

Following the method described in Example 1a, but using the material from Example 11b, there was obtained 3.7 g (41% yield) of the product as a white foam. The structure was confirmed by NMR and mass spectroscopy.

d) Bis-(3-methylphenylmethyl)acetyl-(α-methyl-D-tryptophan)

Following the method outlined in Example 1b, but using the material from Example 11c, there was obtained 3.42 g (98% yield) of the product as a white foam. The structure was confirmed by NMR and mass spectroscopy.

EXAMPLE 12

Bis-2-(1-naphthylmethyl)-2-methylacetyl-(α-methyl-D-tryptophan)

a) Methyl bis-2-(1-naphthylmethyl)-2-methylacetate

A solution of 2.28 g (22.6 mmol) of diisopropylamine in 25 mL THF was cooled in ice and treated with 14.2 mL (22.6 mmol) of a 1.6M solution of n-butyl lithium in hexane. After 15 minutes, the solution was cooled to −78° C. and a solution of 8.0 g (22.6 mmol) of methyl bis-(1-naphthylmethyl)acetate in 80 mL THF added dropwise. After stirring for 1 hour at −78° C. 4.0 mL (62 mmol) of methyl iodide was added. After stirring at −78° C. for 1 hour, the solution was allowed to stir at room temperature overnight. The solution was diluted with EtOAc and washed with 1N HCl, H$_2$O, 10% Na$_2$SO$_3$, saturated NaHCO$_3$, and saturated NaCl. Drying over MgSO$_4$ and removal of the solvent under reduced pressure left 8.3 g of a viscous oil. HPLC analysis showed this to be 80% alkylated. The material was resubmitted to the alkylation conditions. There was obtained 8.3 g (100% yield) of the product as a viscous oil. HPLC analysis showed this to be 97.5% alkylated product. The structure was confirmed by NMR and mass spectroscopy.

b) Bis-2-(1-naphthylmethyl)-2-methylacetic acid

A suspension of 8.3 g (22.6 mmol) of the material from Example 12a in 80 mL ethyleneglycol was treated with a solution of 9.0 g (0.226 mol) of NaOH in 40 mL H$_2$O and heated at reflux overnight. Solution occurs at the reflux temperature. The solution was poured into H$_2$O and acidified with dilute HCl. The solid was collected and recrystallized from CH$_3$CN/H$_2$O to give 5.57 g (69.6% yield) of the product as a cream solid, mp 160°–163° C. The structure was confirmed by NMR and mass spectroscopy.

c) Bis-2-(1-naphthylmethyl)-2-methylacetyl chloride

A solution of 5.44 g (15.3 mmol) of the material from Example 12b in 20 mL SOCl$_2$ was stirred at room temperature overnight. The SOCl$_2$ was removed under reduced pressure, the residue taken up in Et$_2$O, and the solvent again removed. Trituration with Et$_2$O/hexane gave 3.65 g (64% yield) of the product as a tan solid, mp 113°–114° C. The structure was confirmed by mass spectroscopy.

d) Methyl bis-2-(1-naphthylmethyl)-2-methylacetyl-(α-methyl-D-tryptophan)

Following the procedure outlined in Example 1a, but using the material from Example 12c, there was obtained 1.22 g (80.3% yield) of the product as a white foam. The structure was confirmed by NMR and mass spectroscopy.

e) Bis-2-(1-naphthylmethyl)-2-methylacetyl-(α-methyl-D-tryptophan)

Following the procedure outlined in Example 1b, but using the material from Example 12d, there was obtained 1.13 g (100%) yield) of the product as a white foam. The structure was confirmed by NMR and mass spectroscopy.

Analysis calculated for C$_{37}$H$_{34}$N$_2$O$_3$.4H$_8$O$_2$.H$_2$O (MW 660.78): C, 74.52; H, 6.71; N, 4.24. Found: C, 74.84; H, 6.54; N, 3.84.

EXAMPLE 13

Bis-(1-naphthylmethyl)acetyl-(α-methyl-D, L-phenylalanine)

a) Methyl bis-(1-naphthylmethyl)acetyl-(α-methyl-D, L-phenylalanine)

Following the procedure outlined in Example 1a, but using methyl α-methyl-D,L-phenylalanine, there was obtained 1.02 g (36% yield) of the product as an oil. The structure was confirmed by NMR and mass spectroscopy.

b) Bis-(1-naphthylmethyl)acetyl-(α-methyl-D, L-phenylalanine)

Following the procedure outlined in Example 1b, but using the material from Example 13a, there was obtained 0.92 g (100% yield) of the product as a white foam. The structure was confirmed by NMR and mass spectroscopy.

EXAMPLE 14

Bis-(1-naphthylmethyl)acetyl-(α-methyl-D, L-tyrosine)

a) Methyl bis-(1-naphthylmethyl)acetyl-(α-methyl-D, L-tyrosine)

Following the methods of Example 2c, but using bis-(1-naphthylmethyl)acetic acid and methyl α-methyl D, L-tyrosine, there was obtained 0.3 g (19.5% yield) of the product as a white foam. The structure was confirmed by NMR spectroscopy.

b) Bis-(1-naphthylmethyl)acetyl-(α-methyl-D, L-tyrosine)

Following the method of Example 4d, but using the material from Example 14a, gave 0.25 g (85.6% yield) of the product as an amorphous white solid. The structure was confirmed by NMR and mass spectroscopy.

Analysis calculated for $C_{34}H_{31}NO_4 \cdot 0.3H_2O \cdot 0.2C_3H_7NO$ (MW 537.62): C, 77.29; H, 6.19; N, 3.13. Found: C, 77.30; H, 6.27; N, 3.11.

EXAMPLE 15

N-[2-bis-(1-naphthylmethyl)ethyl]-(α-methyl-D-tryptophan)

a) Bis-(1-naphthylmethyl)acetic acid, N,O-dimethyl-hydroxamide

A suspension of 1.36 g (13.9 mmol) of N,O-dimethylhydroxylamine.HCl in 25 mL $CH_2Cl_2$ was treated with 1.7 mL (13.9 mmol) of N-methylpiperidine. This solution was then added to a cold solution of 5.0 g (13.9 mmol) of bis-(1-naphthylmethyl)acetyl chloride in 30 mL $CH_2Cl_2$, followed by 1.7 mL (13.9 mmol) of N-methylpiperidine. The cooling was removed and the solution allowed to stir at room temperature overnight. The solvent was removed under reduced pressure, and the residue taken up in EtOAc and washed with 1N HCl, $H_2O$, saturated $NaHCO_3$, and saturated NaCl. Drying over $MgSO_4$ and removal of the solvent under reduced pressure left the crude product. Chromatography on silica gel, eluting with $CHCl_3$, gave 3.48 g (65.1% yield) of the product as an oil which crystallized on standing, mp 101°–103° C. The structure was confirmed by NMR and mass spectroscopy.

b) Bis-(1-naphthylmethyl)acetaldehyde

A solution of 3.48 g (9.1 mmol) of the product from Example 15a in 15 mL THF was cooled in ice and treated with 0.45 g (11.8 mmol) of lithium aluminum hydride. After stirring at 0° C. for 45 minutes, a solution of 5 g $KHSO_4$ in 30 mL $H_2O$ was added rapidly. The mixture was diluted with EtOAc and washed with 1N HCl, $H_2O$, saturated $NaHCO_3$, and saturated NaCl. Drying over $MgSO_4$ and removal of the solvent under reduced pressure left 2.35 g (79.9% yield) of the product as an oil which crystallized on standing. The structure was confirmed by NMR and mass spectroscopy.

c) Methyl N-[2-bis-(1-naphthylmethyl)ethyl]-(α-methyl-D-tryptophan)

A solution of 2.35 g (7.2 mmol) of bis-(1-naphthylmethyl)acetaldehyde and 1.7 g (7.2 mmol) of methyl α-methyl-D-tryptophan in 30 mL isopropanol and 20 mL THF was stirred with 14 g of 3Å molecular sieves overnight. A trace of bromocresol green was added and the pH adjusted to a pale green with 1N HCl gas in dioxane. The mixture was cooled in ice and 842 mg (12.7 mmol) of $NaCNBH_3$ added and the mixture allowed to stir at room temperature overnight. The mixture was filtered and the filtrate concentrated under reduced pressure. The residue was taken up in EtOAc and washed with saturated $NaHCO_3$, then saturated NaCl. Drying over $MgSO_4$ and removal of the solvent under reduced pressure left the crude product. Chromatography on silica gel, eluting with $CHCl_3$:EtOAc (95:5) gave 0.62 g (15.9% yield) of the product as a white foam. The structure was confirmed by NMR and mass spectroscopy.

d) N-[2-bis-(1-naphthylmethyl)ethyl]-(α-methyl-D-tryptophan)

A solution of 0.62 g (1.1 mmol) of the material from Example 15c in 10 mL dioxane and 5 mL MeOH was treated with 3.0 mL (6 mmol) of 2N NaOH and heated at reflux for 4 hours. The solvent was removed under reduced pressure and the residue mixed with $H_2O$ and 6.0 mL (6 mmol) of 1N HCl added. The mixture was extracted with EtOAc and the EtOAc washed with saturated NaCl. Drying over $MgSO_4$ and removal of the solvent under reduced pressure left the product as a glass. This was taken up in $CH_2Cl_2$, treated with charcoal, filtered, and the solvent removed under reduced pressure to give 315 mg (52.5% yield) of the product as a brown foam. The structure was confirmed by NMR and mass spectroscopy.

Analysis calculated for $C_{36}H_{34}N_2O_2 \cdot 0.5CH_2Cl_2 \cdot H_2O$ (MW 587.13): C, 74.66; H, 6.35; N, 4.77. Found: C, 74.55; H, 6.26; N, 4.55.

EXAMPLE 16

Bis-(cyclohexylmethyl)acetyl-(α-methyl-D-tryptophan)

a) Bis-(cyclohexylmethyl)acetic acid

A solution of 3.0 g (12.5 mmol) of dibenzyl acetic acid in 100 mL of HOAc was treated with 0.5 g $PrO_2$ and reduced with $H_2$ at 25° C., 50 psi. When the required amount of $H_2$ had been taken up, the mixture was filtered and the solvent removed under reduced pressure. Hexane was added and the solvent removed again leaving 3.1 g (98.4% yield) of the product as an oil which crystallized on standing, mp 67°–69° C. The structure was confirmed by NMR and mass spectroscopy.

b) Bis-(cyclohexylmethyl)acetyl chloride

A solution of 2.97 g (11.8 mmol) of bis-(cyclohexylmethyl)acetic acid in 20 mL $SOCl_2$ was stirred at room temperature overnight. The $SOCl_2$ was removed under reduced pressure, the residue taken up in $Et_2O$, and the solvent removed under reduced pressure. The residue was taken up in hexane and the solvent removed under reduced pressure leaving 2.94 g (92.4% yield) of the product as an oil. The structure was confirmed by mass spectroscopy.

c) Methyl bis-(cyclohexylmethyl)acetyl-(α-methyl-D-tryptophan)

To a solution of 0.69 g (3.0 mmol) of methyl α-methyl-D-tryptophan in 20 mL THF was added 0.8 g (3.0 mmol) of bis-(cyclohexylmethyl)acetyl chloride followed by 0.5 mL of $Et_3N$ and the suspension stirred at room temperature for 3 days. The mixture was diluted with EtOAc and washed with 1N citric acid, $H_2O$, and saturated NaCl. Drying over $MgSO_4$ and removal of the solvent under reduced pressure left 1.4 g of the crude product as a foam. Chromatography on silica gel, eluting with $CHCl_3$/EtOAc (95/5) gave 0.91 g (65% yield) of the product as a white foam. The structure was confirmed by NMR and mass spectroscopy.

d) Bis-(cyclohexylmethyl)acetyl-(α-methyl-D-tryptophan)

Following the procedure of Example 16, but using the material from Example 16c, there was obtained 0.96 g (100% yield) of the product as a white foam. The structure was confirmed by NMR and mass spectroscopy.

Analysis calculated for $C_{28}H_{28}N_2O_3 \cdot 0.4C_4H_8O_2$ (MW 475.76): C, 74.72; H, 6.61; N, 5.89. Found: C, 74.32; H, 6.35; N, 5.80.

We claim:

1. A compound of formula

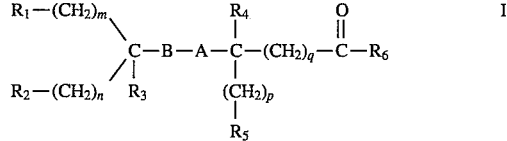

or a pharmaceutically acceptable salt thereof wherein $R_1$ and $R_2$ are each independently a substituted or unsubstituted aryl selected from phenyl, naphthyl, anthracenyl, and fluorenyl a partially or completely saturated compound derived from the said aryl or is a substituted or unsubstituted 3- to 5-membered cycloalkyl wherein the substituents are from 1 to 3 groups selected from alkyl which is a straight or branched chain of from 1 to 6 carbons, alkoxy, the alkyl portion of which is a straight or branched chain of 1 to 6 carbons, hydroxy, or halogen;

m and n are each independently an integer of from 1 to 3;

$R_3$ is hydrogen or a straight or branched alkyl of from 1 to 4 carbon atoms;

B is absent or —CH=CH—, or —(CH$_2$)$_r$ wherein r is an integer of from 1 to 3;

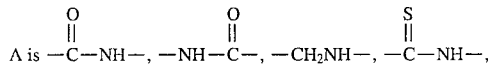

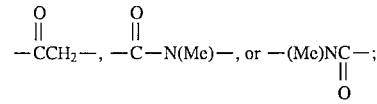

$R_4$ is a straight or branched alkyl of from 1 to 4 carbon atoms, alkenyl of from 2 to 4 carbon atoms, or benzyl or benzyl substituted with 1 to 3 halo, alkoxy, or alkyl groups;

p is an integer of from 0 to 3;

$R_5$ is a substituted or unsubstituted 2- or 3-indolyl;

q is an integer of from 0 to 3; and $R_6$ is $OR_7$ wherein $R_7$ is hydrogen or lower alkyl or $R_6$ is $NR_8R_9$, wherein $R_8$ and $R_9$ are each independently hydrogen or lower alkyl; or $R_8$ and $R_9$ together form a ring selected from pyrrolidine, piperidine, morpholine, and N-methylpiperazine.

2. A compound according to claim 1 wherein $R_1$ and $R_2$ are each independently a substituted or unsubstituted phenyl or naphthyl, or a phenyl or naphthyl which is partially or completely saturated;

m and n are each independently an integer of from 1 to 2;

$R_3$ is hydrogen or methyl;

B is absent;

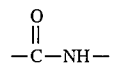

A is —C—NH—
or —CH$_2$NH—;

$R_4$ is a straight or branched alkyl of from 1 to 4 carbon atoms, alkenyl of from 2 to 4 carbon atoms, or benzyl;

p is an integer of from 1 to 2;

$R_5$ is a substituted or unsubstituted 2- or 3-indolyl;

q is an integer of from 0 to 1;

$R_6$ is $OR_7$ or $NR_8R_9$ wherein $R_7$ is hydrogen, $R_8$ and $R_9$ are each independently hydrogen or lower alkyl; or $R_8$ and $R_9$ together form a ring selected from pyrrolidine, piperidine, morpholine and N-methylpiperazine.

3. A compound according to claim 1 wherein $R_1$ and $R_2$ are each independently selected from phenyl, naphthyl, 3,4-methylenedioxyphenyl, 2,3-dimethylphenyl, 5,6,7,8-tetrahydro-1-naphthyl, 2,3,4,5,6-pentafluorophenyl, 2-methylphenyl, 3-methylphenyl, and cyclohexyl;

m and n are each independently an integer of from 1 to 2;

$R_3$ is hydrogen;

B is absent;

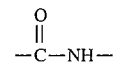

A is —C—NH—
or —CH$_2$NH—;

$R_4$ is methyl;

p is 1;

$R_5$ is 2- or 3-indolyl;

q is an integer of from 0 to 1; and $R_6$ is OH, $NH_2$, $N(CH_3)_2$, or N

4. A compound selected from

Bis-(1-naphthylmethyl)acetyl-(α-methyl-D-tryptophan);

Bis-(3,4-methylenedioxyphenylmethyl)acetyl-(α-methyl-D-tryptophan);

Bis-(2-naphthylmethyl)acetyl-(α-methyl-D-tryptophan);

Bis-(2,3-dimethylphenylmethyl)acetyl-(α-methyl-D-tryptophan);

Bis-(5,6,7,8-tetrahydro-1-naphthylmethyl)acetyl-(α-methyl-D-tryptophan);

Bis-(2,3,4,5,6-pentafluorophenylmethyl)acetyl-(α-methyl-D-tryptophan);

Bis-(1-naphthylmethyl)acetyl-(α-methyl-L-tryptophan);

2-(1-Naphthylmethyl)-2-benzylacetyl-(α-methyl-D-tryptophan);

Bis-(2-methylphenylmethyl)acetyl-(α-methyl-D-tryptophan);

Bis-(3-methylphenylmethyl)acetyl-(α-methyl-D-tryptophan);

Bis- 2-(1-naphthylmethyl)-2-methylacetyl-(α-methyl-D-tryptophan);

Bis-(1-naphthylmethyl)acetyl-(α-methyl-D, L-phenylalanine);

Bis-(1-naphthylmethyl)acetyl-(α-methyl-D, L-tyrosine);

N-[2-bis-(1-naphthylmethyl)ethyl]-(α-methyl-D-tryptophan); and

Bis-(cyclohexylmethyl)acetyl-(α-methyl-D-tryptophan).

5. A compound named Bis-(1-naphthylmethyl)acetyl-(α-methyl-D-tryptophan).

6. A pharmaceutical composition comprising a therapeutically effective amount of a compound according to claim 1 in admixture with a pharmaceutically acceptable excipient, diluent, and/or carrier.

7. A method of inhibiting elevated levels of endothelin comprising administering to a host suffering therefore a therapeutically effective amount of a composition according to claim 1 in unit dosing form.

8. A method of treating subarachnoid hemorrhage comprising administering to a host suffering therefrom a therapeutically effective amount of a compound according to claim 1 in unit dosage form.

9. A method of treating cerebral vasospasm comprising administering to a host suffering therefrom a therapeutically effective amount of a compound according to claim 1 in unit dosage form.

10. A method of treating ischemic disease comprising administering to a host suffering therefrom a therapeutically effective amount of a compound according to claim 1 in unit dosage form.

11. A method of treating stroke comprising administering to a host suffering therefrom a therapeutically effective amount of a compound according to claim 1 in unit dosage form.

12. A method of treating cerebral ischemia comprising administering to a host suffering therefrom a therapeutically effective amount of a compound according to claim 1 in unit dosage form.

* * * * *

UNITED STATES PATENT AND TRADEMARK OFFICE
CERTIFICATE OF CORRECTION

PATENT NO. : 5,610,177
DATED : Mar. 11, 1997
INVENTOR(S) : Doherty et al.

It is certified that error appears in the above-indentified patent and that said Letters Patent is hereby corrected as shown below:

Column 27, line 1, "front" should read "from".

Column 27, line 29, "$K_8$" should read "$R_8$".

Column 27, lines 42-44, delete "$\overset{O}{\underset{\|}{-C-NH-}}$".

Column 27, line 46, "A is -C-NH-" should read "A is $\overset{O}{\underset{\|}{-C-NH-}}$".

Column 28, lines 2-4, delete "$\overset{O}{\underset{\|}{-C-NH-}}$".

Column 28, line 6, "A is -C-NH-" should read "A is $\overset{O}{\underset{\|}{-C-NH-}}$".

Column 28, line 13, delete "N" at the end of the line.

Signed and Sealed this

Tenth Day of April, 2001

Attest:

NICHOLAS P. GODICI

Attesting Officer    Acting Director of the United States Patent and Trademark Office